US00PP32827P2

(12) United States Plant Patent
Winslow et al.

(10) Patent No.: US PP32,827 P2
(45) Date of Patent: Feb. 23, 2021

(54) ***TECOMA* PLANT NAMED 'BALBAHRISE'**

(50) Latin Name: *Tecoma stans*
Varietal Denomination: Balbahrise

(71) Applicant: Ball Horticultural Company, West Chicago, IL (US)

(72) Inventors: Benjamin K. Winslow, Austin, TX (US); Gail Shafer, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/879,039

(22) Filed: May 20, 2020

(51) Int. Cl.
*A01H 5/00* (2018.01)
*A01H 6/00* (2018.01)
*A01H 5/02* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Tecoma* plant named 'Balbahrise', characterized by its dark yellow and greyed yellow-orange colored flowers, dark green-colored foliage, and moderately vigorous, upright growth habit, is disclosed.

1 Drawing Sheet

Latin name of genus and species of plant claimed: *Tecoma stans*.

Variety denomination: 'Balbahrise'.

BACKGROUND OF THE INVENTION

The present invention relates to a new and distinct cultivar of *Tecoma* plant botanically known as *Tecoma stans* and hereinafter referred to by the cultivar name 'Balbahrise'.

The new cultivar originated in a controlled breeding program in Arroyo Grande, Calif. during March 2015. The objective of the breeding program was the development of *Tecoma* cultivars having early continuous flowering and upright, well-branched habits.

The new *Tecoma* cultivar is the result of self-pollination of the proprietary *Tecoma stans* breeding selection coded 19553, not patented, characterized by its dark yellow and greyed yellow-orange colored flowers, dark green-colored foliage, and moderately vigorous, upright growth habit. The new cultivar was selected as a single flowering plant within the progeny of the above stated self-pollination during May 2016 in a controlled environment in Arroyo Grande, Calif.

Asexual reproduction of the new cultivar by terminal stem cuttings since May 2016 in Arroyo Grande, Calif. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbahrise' as a new and distinct cultivar of *Tecoma* plant:

1. Dark yellow and greyed yellow-orange colored flowers;
2. Dark green-colored foliage; and
3. Moderately vigorous, upright growth habit.

Plants of the new cultivar differ from plants of the parent primarily in having more branches per plant and more inflorescences per plant.

Of the many commercially available *Tecoma* cultivars, the most similar in comparison to the new cultivar is Bahama Yellow 'Balbahel', U.S. Plant Pat. No. 30,667. However, in comparison, plants of the new cultivar differ from plants of 'Balbahel' in at least the following characteristic:

1. Plants of the new cultivar have a dark yellow and greyed yellow-orange flower color while plants of 'Balbahel' batter have a medium yellow-colored flower color.
2. Plants of the new cultivar have smaller flowers, as measured by depth and diameter, than plants of 'Balbahel'; and
3. Plants of the new cultivar have more leaflets per leaf than plants of 'Balbahel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbahrise'. The plants were approximately 18 weeks old and were grown for approximately 10 weeks in an outdoor nursery in Elburn, Ill.

DETAILED BOTANICAL DESCRIPTION

Figure 1:
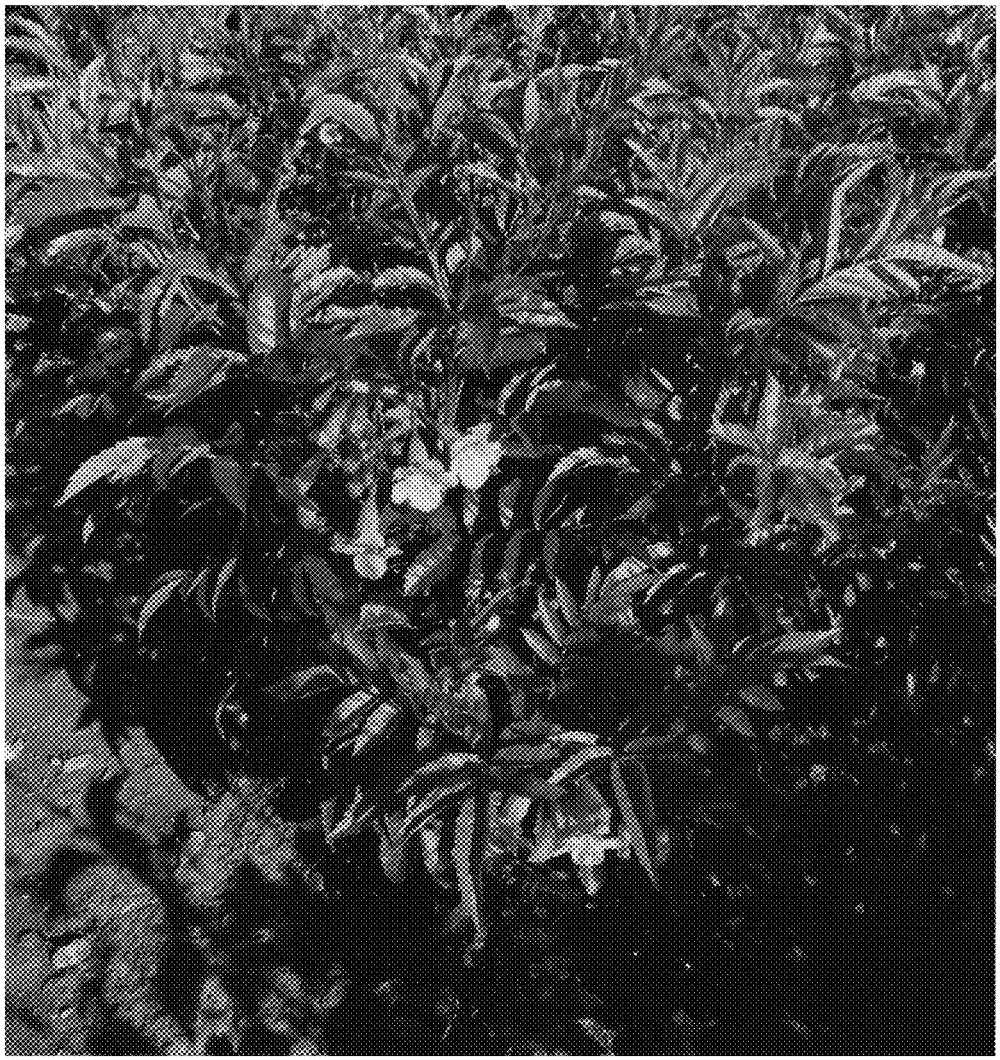
FIG. 1 illustrates a side view of the overall growth and flowering habit of 'Balbahrise'.
Figure 2:
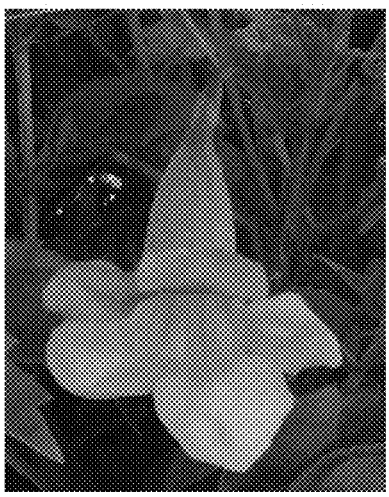
FIG. 2 illustrates a close-up view of an individual flower of 'Balbahrise'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2019 under natural light conditions in West Chicago, Ill.

The following descriptions and measurements describe approximately 18-week-old plants produced from cuttings taken from stock plants. Plants were given one pinch at transplant into a 3.5-inch pot and were grown for 3 weeks before transplant into an outdoor nursery in Elburn, Ill. Plants were then grown for approximately 10 weeks. Measurements and numerical values represent averages of typical plants.

Botanical classification: *Tecoma stans* 'Balbahrise'.

Parentage:

*Female and male parents*.—Proprietary *Tecoma stans* breeding selection coded 19553, not patented.

Propagation:

*Type cutting*.—Softwood cutting.

*Time to initiate roots*.—Approximately 14 to 21 days.

*Time to produce a rooted cutting*.—Approximately 5 to 7 weeks.

*Root description*.—Medium thickness.

*Rooting habit*.—Freely branching; medium density.

Plant description:

*Commercial crop time*.—Approximately 14 to 20 weeks from a rooted cutting to finish in a one-gallon container.

*Growth habit and general appearance*.—Shrub, moderately vigorous, upright.

*Hardiness*.—USDA Zone 8 (10° F. to 20° F.).

*Heat tolerance*.—Regularly tolerates temperatures as high as 40.6° C. (105° F.) in the summer.

*Size*.—Height from soil level to top of plant plane: Approximately 59.0 cm. Width: Approximately 67.0 cm.

*Branching habit*.—Freely branching. Pinching improves basal branching. Aspect: Erect to approximately 45° from center. Quantity of branches per plant: Approximately 2 main stems per plant with approximately 6 lateral branches per stem.

*Lateral branches*.—Strength: Strong. Length to base of peduncle: Approximately 23.0 cm long. Diameter: Approximately 5.0 mm to 8.0 mm. Length of central internode: Approximately 3.2 cm. Texture of young stems: Glabrous with lenticels of approximately 1.0 mm in length. Texture of mature stems: Rough, woody. Color of young stems: 146A with lenticels of 199B. Color of mature stems: 146A tinted with 187A in sun, becoming woody N199B with age.

Foliage description:

*General description*.—Form: Compound, odd-pinnately. Arrangement: Opposite. Fragrance: None detected. Quantity of leaflets per leaf: Approximately 9 to 11.

*Leaves*.—Aspect: Acute to perpendicular to stem. Shape of overall leaf: Ovate. Shape of leaflets: Elliptic to oblong. Margin: Serrate. Apex: Cuspidate. Base: Rounded to oblique. Venation pattern: Pinnate, reticulate. Length of mature leaf: Approximately 15.0 cm. Width of mature leaf: Approximately 13.0 cm. Length of terminal leaflet: Approximately 6.5 cm. Width of terminal leaflet: Approximately 2.7 cm. Length of lateral leaflet: Approximately 6.0 cm. Width of lateral leaflet: Approximately 2.7 cm. Texture of upper surface: Glossy, rugulous. Texture of lower surface: Sparsely pubescent. Color of upper surface of young foliage: 146A with venation color of 146C. Color of lower surface of young and mature foliage: Closest to 146B with venation color of 146C. Color of upper surface of mature foliage: 137A with venation color of 146B.

*Leaf petiole*.—Length: Approximately 4.0 cm. Diameter: Approximately 3.0 mm. Texture: Glabrous. Color of upper and lower surfaces: 146B to 146C.

*Leaflet petiole*.—Length: Approximately 4.0 mm to sessile. Diameter: Approximately 1.0 mm. Texture: Glabrous. Color of upper and lower surfaces: 146B to 146C.

Flowering description:

*Flowering season*.—'Balbahrise' is free flowering under outdoor growing conditions with substantially continuous blooming in warm climates.

*Lastingness of individual inflorescence on the plant*.—Approximately 5 to 7 days.

*General description*.—Terminal panicles. Aspect: Facing upward to outward. Fragrance: Slight, sweet in evening. Quantity inflorescences per plant: Approximately 7. Diameter: Approximately 14.0 cm. Height: Approximately 15.0 cm. Quantity of flowers per inflorescence: Approximately 1 to 4 with up to 9 at peak flower.

*Peduncle*.—Strength: Strong. Shape: Rounded. Aspect: Erect to about 90° from branch axis. Length: Approximately 3.0 cm. Diameter: Approximately 3.0 mm to 4.0 mm. Texture: Sparsely pubescent. Color: 146A.

Flower description:

*General description*.—Type: Salverform, flared trumpet.

*Bud*.—Rate of opening: Generally takes 7 to 10 days for bud to progress from first color to fully open flower.

*Bud just before opening*.—Shape: Obovoid. Depth: Approximately 3.1 cm. Diameter: Approximately 1.0 cm. Color: 172A to 172B with N163C to N163D on dorsal surface.

*Corolla*.—Depth: Approximately 4.5 cm. Diameter: Approximately 3.5 cm.

*Petal lobes*.—Quantity: 5, imbricate near base. Petals are fused at base forming a corolla tube. Shape: Ovate. Appearance: Dull, wavy. Margin: Entire. Apex: Rounded. Length from throat: Approximately 1.2 cm. Width: Approximately 1.7 cm. Texture of upper and lower surfaces: Glabrous. Color of upper surface when first and fully open: 15B with upper petals having an overlay of N163C. Color of lower surface when first and fully open: 15C with upper petals having an overlay of N163B.

*Corolla tube*.—Length: Approximately 3.5 cm. Diameter at tube opening: Approximately 1.2 cm. Diameter at base: Approximately 2.0 mm. Texture of inner surface: Glabrous. Texture of outer surface: Glabrous. Color of inner surface: 15B with throat opening and venation of N163A. Color of outer surface: 15C with an overlay of N163A to N163B primarily on ventral surface.

*Calyx*.—Shape: Cup, with five acute tips. Margin of free portion: Entire, ciliate. Length: Approximately 5.0 mm. Diameter: Approximately 3.0 mm. Texture of inner and outer surfaces: Glabrous. Color of inner and outer surfaces: 144A.

*Pedicel*.—Strength: Strong, flexible. Aspect: At an acute angle. Length: Approximately 5.0 mm. Diameter: Approximately 1.0 mm. Texture: Glabrous. Color: 144A.

*Reproductive organs*.—Androecium: Stamen quantity: 4 per flower, didynamous, adnate to tube, fixed portion glandular pubescent, anthers sparsely pubescent. Stamen length: Longer pair of approximately 3.0 cm and shorter pair of approximately 2.5 cm. Filament length of fixed portion: Approximately 1.0 cm. Filament color: 145D. Anther shape: Divergent. Anther length: Approximately 3.0 mm. Anther color: 8D. Pollen amount: Sparse. Pollen color: 155D. Gynoecium: Pistil quantity: 1 per flower. Pistil length: Approximately 3.0 cm. Stigma shape: Two-lipped. Stigma length: Approximately 2.0 mm. Stigma color: 145B. Style length: Approximately 2.3 cm. Style color: 145C. Ovary length: Approximately 5.0 mm. Ovary color: 144B.

Seed and fruit production: Neither seed nor fruit production has been observed.

Disease and pest resistance: Resistance to pathogens and pests common to *Tecoma* has not been observed.

What is claimed is:

1. A new and distinct cultivar of *Tecoma* plant named 'Balbahrise', substantially as herein illustrated and described.

* * * * *